United States Patent [19]

Schach et al.

[11] Patent Number: 6,057,478
[45] Date of Patent: May 2, 2000

[54] PROCESS FOR PREPARING ARYLHYDRAZINES

[75] Inventors: Thomas Schach, Mumbai, India; Heinrich Volk, Bad Vilbel; Manfred Koch, Eppstein-Niederjosbach, both of Germany

[73] Assignee: Clariant GmbH, Frankfurt, Germany

[21] Appl. No.: 09/314,038

[22] Filed: May 18, 1999

[30] Foreign Application Priority Data

May 19, 1998 [DE] Germany .................... 198 22 316

[51] Int. Cl.[7] .................................. C07C 241/02
[52] U.S. Cl. .................................................. 564/314
[58] Field of Search ............................... 564/314

*Primary Examiner*—Peter O'Sullivan
*Attorney, Agent, or Firm*—Scott E. Hanf

[57] ABSTRACT

The present invention relates to a process for preparing arylhydrazines of the formula $R^1R^2R^3Ar\text{—}NH\text{—}NH_2$ (I) by reacting an arylhydrazinedisulfonate of the formula

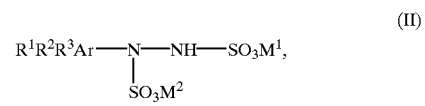

in which $R^1$, $R^2$, and $R^3$ are identical or different and are H, $C_1$–$C_4$-alkyl, $C_1$–$C_4$-alkoxy, halogen or OH, Ar is phenyl or naphthyl, $M^1$ and $M^2$ are identical or different and are H, $NH_4$, an alkali metal or ½ alkaline earth metal and $R^1$, $R^2$, $R^3$ and Ar in the formulae (I) and (II) have the same meaning, with water and an inorganic acid at from 0 to 100° C. in the presence of an inert organic solvent to give the corresponding arylhydrazine salt and treating the arylhydrazine salt with a base.

11 Claims, No Drawings

PROCESS FOR PREPARING ARYLHYDRAZINES

CROSS-REFERENCES TO RELATED APPLICATIONS

The present invention is described in the German priority application No. DE 19 822 316.1, filed May 19, 1998, which is hereby incorporated by reference as is fully disclosed herein The present invention relates to an advantageous process for preparing arylhydrazines by hydrolysis of the corresponding arylhydrazinedisulfonates.

BACKGROUND OF THE INVENTION

Arylhydrazines, in particular phenylhydrazines, play an important role as intermediates in the preparation of crop protection agents (triazolones), pharmaceuticals from the series of the pyrazolones, such as Antipyrin or Pyramidon (Beyer/Walter, Lehrbuch der organischen Chemie, page 588, $21^{st}$ edition (1988), S. Hirzel Verlag Stuttgart) and pyrazolone dyes.

Hitherto, the most important route for preparing arylhydrazines, in particular phenylhydrazines, used the corresponding arylamines. This type of synthesis is demonstrated below, using the preparation of phenylhydrazine starting from aniline as an example. The synthesis route is summarized schematically in abbreviated form by the following equations (1) to (4):

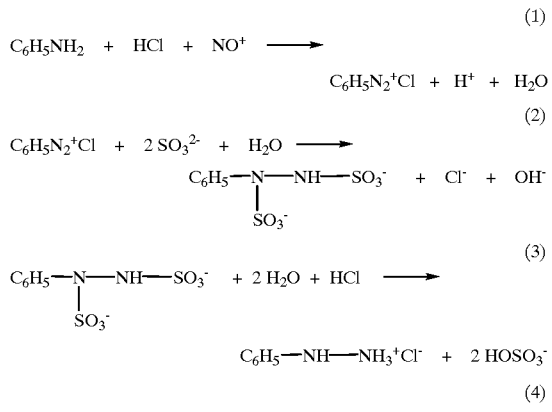

As can be seen from equation (1), aniline is converted into the corresponding diazonium salt which, according to equation (2), is reduced to the corresponding phenylhydrazinedisulfonate using alkali metal sulfite. The phenylhydrazinedisulfonate is subsequently, according to equation (3), hydrolyzed with a mineral acid where, however, not the phenylhydrazine but the corresponding phenylhydrazine salt is formed from which, as described in equation (4), the phenylhydrazine can be liberated using a base, for example NaOH. This manner of preparing phenylhydrazine is described in Houben-Weyl, Methoden der organischen Chemie, volume 10/2, pp. 180 to 191, in particular p. 181 (1967), fourth edition, Georg Thieme Verlag, Stuttgart.

All the reaction steps described in equations (1) to (4) are carried out in the solvent water. In particular, the hydrolysis described by equation (3), which is carried out using aqueous mineral acid, takes place in the presence of water.

Since the intermediates obtained in accordance with equations (1) to (3) are generally salts, i.e. a diazonium salt in equation (1), a hydrazine disulfonate in equation (2) and a hydrazine salt in equation (3), which are generally considered as being readily water-soluble, it appears neither useful nor sensible to use an additional solvent.

In general, the hydrolysis described in equation (3) requires an appropriate excess of mineral acid, which may be very high for a number of cases. However, a high excess of mineral acid also leads to a high loading of the wastewater produced in the hydrolysis, and to corrosion problems in the reactor vessels used for the hydrolysis. A high proportion of mineral acid in the wastewater furthermore leads to a considerable increase of the costs for wastewater disposal and to increased technical expenditure for regenerating the mineral acid.

SUMMARY OF THE INVENTION

There is therefore a need for a process which avoids the disadvantages mentioned above and which can additionally also be realized on an industrial scale, without requiring great expenditure on apparatus.

Surprisingly, this object is achieved by a process for preparing arylhydrazines of the formula $R^1R^2R^3Ar$—NH—$NH_2$ (I) by reacting an arylhydrazinedisulfonate of the formula

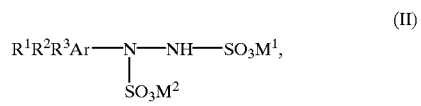

in which $R^1$, $R^2$, and $R^3$ are identical or different and are H, $C_1$–$C_4$-alkyl, $C_1$–$C_4$-alkoxy, halogen or OH, Ar is phenyl or naphthyl, $M^1$ and $M^2$ are identical or different and are H, $NH_4$, an alkali metal or ½ alkaline earth metal and $R^1$, $R^2$, $R^3$ and Ar in the formulae (I) and (II) have the same meaning, with water and an inorganic acid at from 0 to 100° C. in the presence of an inert organic solvent to give the corresponding arylhydrazine salt and treating the arylhydrazine salt with a base.

DESCRIPTION OF THE PREFERRED EMBODIMENTS

In an unexpected manner, the presence of the solvent during the hydrolysis of the arylhydrazinedisulfonate of the formula (II) leads to advantages during the hydrolysis. Thus, in a number of cases, in particular in the case of unstable arylhydrazine salts, the amount of mineral acid that has to be employed can be reduced. Furthermore, the yield and the purity of the arylhydrazine are also improved.

It is possible to employ, with good results, an arylhydrazinedisulfonate of the formula (II), in which Ar is phenyl, the process according to the invention.

It is possible to employ an arylhydrazinedisulfonate of the formula (II) in which $R^1$, $R^2$, $R^3$ are identical or different and are H, $C_1$–$C_4$-alkyl, halogen or OH, in particular H, halogen or OH. Suitable halogens are, in particular, F, Cl or Br, preferably F or Cl.

In particular, it is possible to use an arylhydrazinedisulfonate in which one or two radicals $R^1$, $R^2$ and $R^3$ are OH or halogen, in particular in which one of the radicals $R^1$, $R^2$ and $R^3$ is OH or halogen, for the process according to the invention.

Suitable arylhydrazinedisulfonates of the formula (II) are those in which $M^1$ and $M^2$ are identical or different and are H, $NH_4$ or an alkali metal, in particular H, $NH_4$, Na or K, preferably Na or K, particularly preferably Na.

A particular embodiment of the present invention relates to a process for preparing 2,4-dichloro-5-hydroxyphenylhydrazine by reacting 2,4-dichloro-5-hydroxyphenylhydrazinedisulfonate with water and a mineral acid at from 0 to 100, in particular from 30 to 70,° C. in the presence of an inert organic solvent to give the corresponding 2,4-dichloro-5-hydroxyphenylhydrazine salt, separating off the 2,4-dichloro-5-hydroxyphenylhydrazine salt and reacting it with a base.

Here, the 2,4-dichloro-5-hydroxyphenylhydrazine corresponds to the arylhydrazine of the formula (I), and the 2,4-dichloro-5-hydroxyphenylhydrazinedisulfonate corresponds to the arylhydrazinedisulfonate of the formula (II).

The arylhydrazinedisulfonate of the formula (II) employed is in particular 2,4-dichloro-5-hydroxyphenylhydrazinedisulfonate in which $M^1$ and $M^2$ are identical or different and are H, $NH_4$ or an alkali metal, in particular H, $NH_4$, Na or K, preferably Na or K, particularly preferably Na.

The 2,4-dichloro-5-hydroxyphenylhydrazine salt can be separated off as a solid or, preferably, as the organic phase which contains the 2,4-dichloro-5-hydroxyphenylhydrazine salt dissolved in the organic solvent.

For the process according to the invention, from 2 to 2000 mol of water are usually employed per mole of arylhydrazinedisulfonate of the formula (II). In a large number of cases, it has been found to be useful to use from 20 to 1200, in particular from 50 to 1100, preferably from 100 to 1000 mol of water per mole of arylhydrazinedisulfonate.

Mineral acids are suitable inorganic acids. The inorganic acid employed can be HCl, $H_2SO_4$, $H_3PO_4$, in an anhydrous state or in an aqueous solution. It is particularly simple to use an aqueous solution of the inorganic acid.

A suitable inorganic acid is gaseous HCl or an aqueous HCl solution. The process can be carried out in a particularly simple manner by using an aqueous HCl solution, in particular a 5–33% strength aqueous HCl solution.

From 1 to 30, in particular from 2 to 20, preferably from 4 to 10, mol of inorganic acid per mole of arylhydrazinedisulfonate are employed.

The inert organic solvent is understood as an organic solvent which is inert under the reaction conditions.

Suitable for use as an inert organic solvent are a aliphatic hydrocarbon having from 5 to 25 carbon atoms, an aromatic hydrocarbon having from 6 to 12 carbon atoms, an aliphatic alcohol having from 1 to 12 carbon atoms, a polyalkylene glycol having from 2 to 6 carbon atoms per alkylene, a dialkyl ether having from 2 to 20 carbon atoms per alkyl, a polyalkylene glycol dialkyl ether having from 1 to 6 carbon atoms per alkylene and from 1 to 4 carbon atoms per alkyl, a $C_1$–$C_4$-alkyl ester of an aliphatic $C_1$–$C_6$-carboxylic acid, an aliphaticdi-($C_1$–$C_4$-alkyl)-$C_1$–$C_6$-carboxamide, a nitrile, a dialkyl sulfoxide having from 1 to 4 carbon atoms per alkyl, a dialkylsulfone having from 1 to 4 carbon atoms per alkyl, an imidazolinone, a pyrrolidone or a mixture of these.

Suitable inert organic solvents are methanol, ethanol, n-propanol, isopropanol, n-butanol, isobutanol, tert-butanol, n-pentanol, isopentanol, n-hexanol, isohexanol, n-octanol, isooctanol, n-decanol, isodecanol, n-dodecanol, ethylene glycol, glycerol, diethylene glycol, tetraethylene glycol, diethylene glycol dimethyl ether, tetraethylene glycol dimethyl ether, dimethylformamide, diethylformamide, dimethylacetamide or a mixture of these, in particular methanol, ethanol, n-propanol, isopropanol, n-butanol, isobutanol, tert-butanol, n-pentanol, isopentanol, n-hexanol, isohexanol, n-octanol, isooctanoi, n-decanol, isodecanol or a mixture of these.

Particularly suitable inert organic solvents are n-butanol, isobutanol, n-pentanol, isopentanol, n-hexanol, isohexanol, n-octanol, isooctanol, n-decanol, isodecanol or a mixture of these. In some cases, for example, n-butanol, isobutanol, n-pentanol, isopentanol, n-hexanol, isohexanol, n-octanol, isooctanol or a mixture of these, in particular n-butanol, isobutanol, n-pentanol, isopentanol, n-hexanol, isohexanol or a mixture of these, preferably n-butanol, isobutanol, n-pentanol, isopentanol or a mixture of these have been found to be useful inert organic solvents.

In general, from 0.01 to 100 mol of inert organic solvent are employed per mole of arylhydrazinedisulfonate used. In a large number of cases, it has been found useful to employ from 1 to 50, in particular from 10 to 30, mol of inert organic solvent per mole of arylhydrazinedisulfonate used.

The inert organic solvent can have two different effects. On the one hand, it can accelerate the reaction (hydrolysis), and on the other hand, it can extract the arylhydrazine salt formed, from the aqueous phase, even during the formation.

If it is desired to accelerate the reaction (hydrolysis), ethylene glycol, glycerol, diethylene glycol, tetraethylene glycol, diethylene glycol dimethyl ether, tetraethylene glycol dimethyl ether, dimethylformamide, dimethylacetamide or a mixture of these, in particular ethylene glycol, diethylene glycol, diethylene glycol dimethyl ether, can be employed with good results.

This acceleration of the reaction can be achieved even with relatively small amounts of solvent. Here, it is customary to employ from 0.1 to 5, in particular from 0.5 to 3, mol of inert organic solvent per mole of arylhydrazinedisulfonate used.

If it is intended to extract the arylhydrazine salt from the aqueous phase as early as during its formation in the hydrolysis, aliphatic alcohols having 4 to 10 carbon atoms, for example n-butanol, isobutanol, n-hexanol, n-decanol, can be used with good results.

To carry out this extraction, appropriate amounts of the inert organic solvent are added. In general, from 1 to 50, in particular from 5 to 30, preferably from 10 to 20, mol of inert organic solvent are employed per mole of arylhydrazinedisulfonate used.

It has been found advantageous to initially charge water, the inorganic acid and the inert organic solvent and to add the arylhydrazinedisulfonate of the formula (II).

When carrying out the reaction, it is recommended to choose the rate of addition of the arylhydrazinedisulfonate to water, inorganic acid and inert organic solvent appropriately. Too high a rate of addition of the arylhydrazinedisulfonate can result in a reduction in the yield of arylhydrazine. On the laboratory scale, it has been found to be sufficient to add the arylhydrazinedisulfonate over a period of from 5 minutes to 5 hours, in particular from 10 minutes to 3 hours.

The water, the inorganic acid and the inert organic solvent are heated with stirring to the desired reaction temperature, and the arylhydrazinedisulfonate is then added. It is particularly advantageous to use the arylhydrazinedisulfonate in the form of an aqueous solution.

In a large number of cases, a reaction temperature of from 10 to 90, in particular from 40 to 80,° C. has been found to be sufficient.

During the addition of the arylhydrazinedisulfonate and the subsequent reaction, it has to be ensured that the reaction mixture being formed is mixed well.

Following the hydrolysis of the arylhydrazinedisulfonate, product is in the form of the corresponding arylhydrazine salt, which remains in the reaction mixture or is separated off from the reaction mixture.

The arylhydrazine salt can be separated off as organic phase, which contains the arylhydrazine salt dissolved in the inert organic solvent. This is achieved by simple phase separation and represents a particularly favorable variant of the process according to the invention.

It is also possible to separate off the arylhydrazine salt as a solid, for example by filtration, sedimentation or centrifugation.

By addition of the base, the arylhydrazine is subsequently liberated from the arylhydrazine salt which has been separated off, or from the reaction mixture containing the arylhydrazine salt. Suitable bases are alkali metal oxides, alkali metal hydroxides, alkali metal carbonates, alkaline earth metal oxides, alkaline earth metal hydroxides, in solid form or in the form of aqueous solutions.

It is particularly simple to treat the arylhydrazine salt with an aqueous solution of alkali metal hydroxide, in particular with an aqueous NaOH and/or KOH solution, preferably an aqueous NaOH solution.

The base is usually added at from 0 to 50, in particular from 5 to 40,° C.

The process according to the invention can be carried out continuously or batchwise, in particular batchwise.

The examples below illustrate the present invention in more detail, without limiting it.

EXAMPLES

Experimental part

Example 1

Preparation of 2,4-dichloro-5-hydroxyphenylhydrazine with addition of n-butanol, at 50° C.

In a 4 l four-necked flask fitted with dropping funnel, stirrer and condenser, 417.8 g of aqueous HCl (30% strength), corresponding to 3.4 mol of HCl, and 422.4 9 of n-butanol (saturated with water, approximately 80% strength), corresponding to 4.6 mol of n-butanol, are initially charged. The solution is heated to 50° C. and, over a period of 2 hours, admixed with a total of 1394.6 g of an aqueous solution of 2,4-dichloro-5-hydroxyphenylhydrazinedisulfonate (10.3% strength), corresponding to 0.36 mol of disodium 2,4-dichloro-5-hydroxyphenyl-hydrazinedisulfonate. The reaction solution is kept at 50° C. for another 60 minutes. During the reaction, the reaction system forms two phases, an upper organic phase and a lower aqueous phase. The two phases are separated in a 4 l separating funnel. The aqueous phase is subsequently extracted three times with 50 ml of butanol each time. The organic phases are combined and adjusted to pH 2–2.5 using aqueous sodium hydroxide solution (33% strength), and the aqueous phase that is formed during this operation is also separated off. After the addition of 142 g of water, the pH is adjusted to 6.3–6.9 using aqueous sodium hydroxide solution (33% strength), and the crystalline 2,4-dichloro-5-hydroxyphenylhydrazine is filtered off with suction at 15–20° C. as an orange solid, using a 500 ml suction filter, is washed with 218 g of butanol and dried.

Yield: 68.9 g (0.34 mol) of 2,4-dichloro-5-hydroxyphenylhydrazine (96% pure), this corresponds to a theoretical yield of 96.0%, based on the 2,4-dichloro-5-hydroxyphenylhydrazinedisulfonate employed.

The yield is significantly higher than the yield obtained in the Comparative Example 1.

Example 1A

Preparation of 2,4-dichloro-5-hydroxyphenylhydrazine with addition of ethylene glycol, at 50° C.

In a 4 l four-necked flask fitted with dropping funnel, stirrer and condenser, 417 g (3.4 mol) of 30% strength HCl and 58 g (0.93 mol) of ethylene glycol are initially charged. The solution is heated to 50° C. and, over a period of 2 hours, admixed with a total of 1394.6 g (0.36 mol) of 10.3% strength 2,4-dichloro-5-hydroxyphenyl-hydrazinedisulfonate. The reaction solution is kept at 50° C. for a further 60 minutes and subsequently cooled to room temperature. Immediately after the metered addition has started, a clear solid crystallizes out of the reaction solution. A very voluminous crystal slurry is formed which is filtered off, after cooling to 15–20° C., using a 1 l suction filter.

Yield: 121.0 g (0.19 mol) of 2,4-dichloro-5-hydroxyphenylhydrazine hydrochloride (35.0% pure), this corresponds to a theoretical yield of 51.8%, based on the 2,4-dichloro-5-hydroxyphenylhydrazinedisulfonate employed.

The 2,4-dichloro-5-hydroxyphenylhydrazine hydrochloride obtained is subsequently taken up in water, and the mixture is adjusted to pH 6.3–6.8 using 33% strength NaOH. The precipitate that forms is subsequently separated off in a 250 ml suction filter, washed with water and dried.

Yield: 38.8 g (0.18 mol) of 2,4-dichloro-5-hydroxyphenylhydrazine (90% pure), this corresponds to a theoretic yield of 50.3%, based on the 2,4-dichloro-5-hydroxyphenylhydrazinedisulfonate employed, and of 96.0%, based on the intermediately isolated 2,4-dichloro-5-hydroxyphenylhydrazine hydrochloride.

The yield is significantly higher than the yield obtained in the Comparative Example 1.

Comparative Example 1

Preparation of 2,4-dichloro-5-hydroxyphenylhydrazine without addition of solvent, at 50° C.

In a 4 l four-necked flask fitted with dropping funnel, stirrer and condenser, 417 g of aqueous HCl (30% strength), corresponding to 3.4 mol, are initially charged. The HCl (30% strength) is heated to 50° C. and, over a period of 2 hours, admixed with a total of 1394.6 g of an aqueous solution of 2,4-dichloro-5-hydroxyphenyl-hydrazinedisulfonate (10.3% strength), corresponding to 0.36 mol. The reaction solution is kept at 50° C. for another 60 minutes and subsequently cooled to room temperature. Immediately after the start of the metered addition, a clear solid crystallizes out of the reaction solution. A very voluminous crystal slurry is formed which, after cooling to 15–20° C., is filtered off using a 1 l suction filter. Yield: 109.1 g (0.154 mol) of 2,4-dichloro-5-hydroxyphenylhydrazine hydrochloride (32.0% pure), this corresponds to a theoretical yield of 42.7%, based on the 2,4-dichloro-5-hydroxyphenylhydrazinedisulfonate employed.

The 2,4-dichloro-5-hydroxyphenylhydrazine hydrochloride obtained is subsequently taken up in water and the pH of the mixture is adjusted to 6.3–6.8 using aqueous NaOH (33% strength). The precipitate that forms is subsequently separated off in a 100 ml suction filter, washed with water and dried.

Yield: 31.3 g (0.147 mol) of 2,4-dichloro-5-hydroxyphenylhydrazine (91% pure), this corresponds to a theoretical yield of 41.0%, based on the 2,4-dichloro-5-hydroxyphenylhydrazinedisulfonate employed.

Example 2

Preparation of 2,4-dichloro-5-hydroxyphenylhydrazine with addition of n-butanol, at 60° C.

In a 4 l four-necked flask fitted with dropping funnel, stirrer and condenser, 417.8 g of aqueous HCl (30% strength), corresponding to 3.4 mol of HCl, and 422.4 g of n-butanol (saturated with water, approximately 80% strength), corresponding to 4.6 mol of n-butanol, are initially charged. The solution is heated to 60° C. and, over a period of 15 minutes, admixed with a total of 1394.6 g of an aqueous solution of 2,4-dichloro-5-hydroxyphenylhydrazinedisulfonate (10.3% strength), corresponding to 0.36 mol. The reaction solution is kept at 60° C. for another 60 minutes, and subsequently quickly cooled to 40° C. During the reaction, the reaction system forms two phases, an upper organic phase and a lower aqueous phase. The two phases are separated in a 4 l separating funnel. The aqueous phase is subsequently extracted three times with 50 ml of butanol each time. The organic phases are combined and adjusted to pH 2–2.5 using aqueous sodium hydroxide solution (33% strength), and the aqueous phase that is formed during this operation is also separated off. After the addition of 142 g of water, the pH is adjusted to 6.3–6.9 using aqueous sodium hydroxide solution (33% strength), and the crystalline 2,4-dichloro-5-hydroxyphenylhydrazine is filtered off with suction at 15–20° C. as an orange solid, using a 500 ml suction filter, is washed with 218 g of butanol and dried.

Yield: 64.7 g (0.31 mol) of 2,4-dichloro-5-hydroxyphenylhydrazine (93% pure), this corresponds to a theoretical yield of 87%, based on the 2,4-dichloro-5-hydroxyphenylhydrazinedisulfonate employed. The yield has to be compared with the result of Comparative Example 2 (no isolatable yield).

Comparative Example 2

Preparation of 2,4-dichloro-5-hydroxyphenylhydrazine without addition of solvent, at 60° C.

In a 4 l four-necked flask fitted with dropping funnel, stirrer and condenser, 417.8 g of aqueous HCl (30% strength), corresponding to 3.4 mol, are initially charged. The HCl (30% strength) is heated to 60° C. and, over a period of 15 minutes, admixed with a total of 1394.6 g of an aqueous solution of 2,4-dichloro-5-hydroxyphenylhydrazinedisulfonate (10.3% strength), corresponding to 0.36 mol. The reaction solution is kept at 60° C. for another 2 hours and subsequently cooled to room temperature. As early as during the metered addition, the color of the reaction solution turns to a deep brown, and at the end of the additional stirring time, small amounts of a tar-like residue can be isolated.

Yield: No isolatable 2,4-dichloro-5-hydroxyphenylhydrazine hydrochloride.

Example 3

Preparation of 2,4-dichloro-5-hydroxyphenylhydrazine with addition of n-butanol, at 70° C.

In a 4 l four-necked flask fitted with dropping funnel, stirrer and condenser, 417.8 g of aqueous HCl (30% strength), corresponding to 3.4 mol, and 422.4 g of n-butanol (saturated with water, approximately 80% strength), corresponding to 4.6 mol, are initially charged. The solution is heated to 70° C. and, over a period of 10 minutes, admixed with a total of 1394.6 g of an aqueous solution of 2,4-dichloro-5-hydroxyphenylhydrazinedisulfonate (10.3% strength), corresponding to 0.36 mol. The reaction solution is kept at 70° C. for a further 45 minutes. During the reaction, the reaction system forms two phases, an upper organic phase and a lower aqueous phase. The two phases are separated in a 4 l separating funnel. The aqueous phase is subsequently extracted three times with 50 ml of butanol each time. The organic phases are combined and adjusted to pH 2–2.5 using aqueous sodium hydroxide solution (33% strength), and the aqueous phase that is formed during this operation is also separated off. After the addition of 142 g of water, the pH is adjusted to 6.3–6.9 using aqueous sodium hydroxide solution (33% strength), and the crystalline 2,4-dichloro-5-hydroxyphenylhydrazine is filtered off with suction at 15–20° C. as an orange solid, using a 500 ml suction filter, is washed with 218 g of butanol and dried.

Yield: 70.2 g (0.34 mol) of 2,4-dichloro-5-hydroxyphenylhydrazine (93.1% pure), this corresponds to a theoretical yield of 94.5%, based on the 2,4-dichloro-5-hydroxyphenylhydrazinedisulfonate employed.

The yield has to be compared with the result of Comparative Example 3 (no isolatable yield).

Comparative Example 3

In a 4 l four-necked flask fitted with dropping funnel, stirrer and condenser, 417.8 g of aqueous HCl (30% strength) are initially charged. The HCl (30% strength) is heated to 70° C. and, over a period of 15 minutes, admixed with a total of 1394.6 g of an aqueous solution of 2,4-dichloro-5-hydroxyphenylhydrazinedisulfonate (10.3% strength). The reaction solution is kept at 70° C. for another 45 minutes and subsequently cooled to room temperature. As early as during the metered addition, the color of the reaction solution changes to a deep brown, and at the end of the additional stirring time, it is possible to isolate only polymeric decomposition products.

Yield: no isolatable 2,4-dichloro-5-hydroxyphenylhydrazine hydrochloride.

Example 4

Preparation of 2-fluorophenylhydrazine with addition of n-butanol

In a 2 l four-necked flask fitted with dropping funnel, stirrer and condenser, 240 g of HCl 30% strength and 180 g of n-butanol (saturated with water, approximately 80% strength) are initially charged. The solution is heated to 50° C. and, over a period of 25 minutes, admixed with a total of 1291 g of an aqueous solution of 2-fluorophenylhydrazinedisulfonate—prepared by diazotization of 111 g (1 mol) of 2-fluoroaniline (156 g of water, 303 g of HCl 30% strength, 170 g of NaNO$_2$) and subsequent reduction with sulfite (560 g of NaHSO$_3$+100 g of NaOH). The reaction solution is kept at 50° C. for another 60 minutes. During the reaction, the reaction system forms two phases. The two phases are separated from one another in a 2 l separating funnel. The aqueous phase is subsequently extracted three times with 10 ml of n-butanol each time. The organic phases are combined and adjusted to pH 8.5 using aqueous sodium hydroxide solution (33% strength), and the aqueous phase that forms is also separated off. The solvent is subsequently concentrated until a viscous crystal slurry is formed.

Yield: 98.2 g (0.74 mol) of 2-fluorophenylhydrazine (95% pure), this corresponds to a theoretical yield of 74.0%, based on the 2-fluoroaniline employed.

Example 5

Preparation of 4-chlorophenylhydrazine with addition of n-butanol

In a 2 l four-necked flask fitted with dropping funnel, stirrer and condenser, 95 g of HCl 30% strength and 57 g of n-butanol (saturated with water, approximately 80% strength) are initially charged. The solution is heated to 50°

C. and, over a period of 2 hours, admixed with a total of 720 g of an aqueous solution of 4-chlorophenylhydrazinedisulfonate- prepared by diazotization of 34.4 g (0.27 mol) of 4-chloroaniline (100 g of water, 78 g of HCl 30% strength, 55 g of NaNO$_2$) and subsequent reduction with sulfite (186 g of NaHSO$_3$+57 g of NaOH). The reaction emulsion is kept at 50° C. for another 60 minutes, the pH is adjusted to 6.9 using 119 g of aqueous sodium hydroxide solution 33% strength, and the aqueous phase that is formed is separated off. The aqueous phase is extracted three times with 5 ml of n-butanol each time, and the combined organic phases are cooled to 15° C. The 4-chlorophenylhydrazine that is formed is filtered off with suction at 15° C. as a crystalline solid, using a 500 ml suction filter, washed with 50 ml of n-butanol and dried.

Yield: 36.2 g (0.21 mol) of 4-chlorophenylhydrazine (82.5% pure), this corresponds to a theoretical yield of 78.0%, based on the 4-chloroaniline employed.

We claim:

1. A process for preparing arylhydrazines of the formula R$^1$R$^2$R$^3$Ar—NH—NH$_2$ (I) by reacting an arylhydrazinedisulfonate of the formula

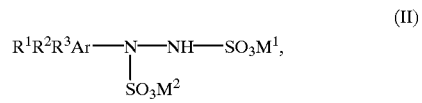

in which R$^1$, R$^2$, and R$^3$ are identical or different and are H, C$_1$–C$_4$-alkyl, C$_1$–C$_4$-alkoxy, halogen or OH, Ar is phenyl or naphthyl, M$^1$ and M$^2$ are identical or different and are H, NH$_4$, an alkali metal or ½ alkaline earth metal and R$^1$, R$^2$, R$^3$ and Ar in the formulae (I) and (II) have the same meaning, with water and an inorganic acid at from 0 to 100° C. in the presence of an inert organic solvent to give the corresponding arylhydrazine salt and treating the arylhydrazine salt with a base.

2. The process as claimed in claim 1, wherein an arylhydrazinedisulfonate of the formula (II), in which Ar is phenyl, is employed.

3. The process as claimed in claim 1, wherein an arylhydrazinedisulfonate of the formula (II), in which one or two radicals R$^1$, R$^2$ and R$^3$ are OH or halogen, is employed.

4. The process as claimed in claim 1, wherein the arylhydrazinedisulfonate of the formula (II) employed is 2,4-dichloro-5-hydroxyphenylhydrazinedisulfonate in which M$^1$ and M$^2$ are identical or different and are H, NH$_4$ or an alkali metal.

5. The process as claimed in claim 1, wherein from 2 to 2000 mol of water are employed per mole of arylhydrazinedisulfonate.

6. The process as claimed in claim 1, wherein the inorganic acid employed is HCl, H$_2$SO$_4$, H$_3$PO$_4$, in an anhydrous state or in an aqueous solution.

7. The process as claimed in claim 1, wherein from 1 to 30 mol of inorganic acid are employed per mole of arylhydrazinedisulfonate.

8. The process as claimed in claim 1, wherein the inert organic solvent used is an aliphatic hydrocarbon having from 5 to 25 carbon atoms, an aromatic hydrocarbon having from 6 to 12 carbon atoms, an aliphatic alcohol having from 1 to 12 carbon atoms, a polyalkylene glycol having from 2 to 6 carbon atoms per alkylene, a dialkyl ether having from 2 to 20 carbon atoms per alkyl, a polyalkylene glycol dialkyl ether having from 1 to 6 carbon atoms per alkylene and from 1 to 4 carbon atoms per alkyl, a C$_1$–C$_4$-alkyl ester of an aliphatic C$_1$–C$_6$-carboxylic acid, an aliphaticdi-(C$_1$–C$_4$-alkyl)-C$_1$–C$_6$-carboxamide, a nitrile, a dialkyl sulfoxide having from 1 to 4 carbon atoms per alkyl, a dialkylsulfone having from 1 to 4 carbon atoms per alkyl, an imidazolinone, a pyrrolidone or a mixture of these.

9. The process as claimed in claim 1, wherein the inert organic solvent used is methanol, ethanol, n-propanol, isopropanol, n-butanol, isobutanol, tert-butanol, n-pentanol, isopentanol, n-hexanol, isohexanol, n-octanol, isooctanol, n-decanol, isodecanol, n-dodecanol, ethylene glycol, glycerol, diethylene glycol, tetraethylene glycol, diethylene glycol dimethyl ether, tetraethylene glycol dimethyl ether, dimethylformamide, diethylformamide, dimethylacetamide or a mixture of these.

10. The process as claimed in claims 1, wherein the inert organic solvent used is methanol, ethanol, n-propanol, isopropanol, n-butanol, isobutanol, tert-butanol, n-pentanol, isopentanol, n-hexanol, isohexanol, n-octanol, isooctanol, n-decanol, isodecanol or a mixture of these.

11. The process as claimed in claim 1, wherein the arylhydrazine salt is separated off as organic phase containing the arylhydrazine salt dissolved in the organic solvent.

* * * * *